(12) United States Patent
Kingsford et al.

(10) Patent No.: US 12,417,818 B1
(45) Date of Patent: Sep. 16, 2025

(54) TOTAL MUTATIONAL BURDEN (TMB) ESTIMATE

(71) Applicant: Ocean Genomics, Inc., Pittsburgh, PA (US)

(72) Inventors: Carleton Kingsford, Pittsburgh, PA (US); Robert Patro, Brookville, MD (US)

(73) Assignee: Ocean Genomics, Inc., Pittsburgh, PA (US)

( * ) Notice: Subject to any disclaimer, the term of this patent is extended or adjusted under 35 U.S.C. 154(b) by 924 days.

(21) Appl. No.: 17/534,803

(22) Filed: Nov. 24, 2021

Related U.S. Application Data (60) Provisional application No. 63/117,792, filed on Nov. 24, 2020.

(51) Int. Cl.
| | |
|---|---|
| *G16B 5/20* | (2019.01) |
| *G06N 7/01* | (2023.01) |
| *G16B 20/50* | (2019.01) |
| *G16B 40/00* | (2019.01) |
| *G16H 50/30* | (2018.01) |

(52) U.S. Cl.
CPC .............. *G16B 5/20* (2019.02); *G06N 7/01* (2023.01); *G16B 20/50* (2019.02); *G16B 40/00* (2019.02); *G16H 50/30* (2018.01)

(58) Field of Classification Search
CPC .......... G16B 5/20; G16B 20/50; G16B 40/00; G06N 7/01; G16H 50/30
See application file for complete search history.

(56) References Cited

U.S. PATENT DOCUMENTS

| | | | |
|---|---|---|---|
| 2019/0256924 A1* | 8/2019 | Vogelstein | C12Q 1/6869 |
| 2020/0105375 A1* | 4/2020 | Pan | G16B 40/20 |
| 2022/0093217 A1* | 3/2022 | Abraham | G16H 10/40 |
| 2023/0223121 A1* | 7/2023 | Colley | G16B 30/00 |
| | | | 705/2 |

OTHER PUBLICATIONS

Kristensen et al., "TMB: Automatic Differentiation and Laplace Approximation", Journal of Statistical Software, Apr. 2016, pp. 1-21, vol. 70, Issue 5.

Budczies et al., "Optimizing Panel-Base Tumor Mutational Burden (TMB) Measurement", Jul. 3, 2019, pp. 1496-1506, vol. 30, Issue 9.

Guo et al., "An Exon Signature to Estimate the Tumor Mutational Burden of Right-sided Colon Cancer Patients", Journal of Cancer, Jan. 2020, pp. 883-892, vol. 11.

Devarakonda et al., "Tumor Mutation Burden as a Biomarker in Resected Non-Small-Cell Lung Cancer", Journal of Clinical Oncology, Oct. 20, 2018, pp. 2995-3008, vol. 36, No. 30.

Martinez-Perez et al., "Panels and Models for Accurate Prediction of Tumor Mutation Burden in Tumor Samples", 2021, pp. 1-8.

Dinsdale, "Methods for Preferential Sampling in Geostatistics", 2013, pp. 1-24 and pp. 1-168.

\* cited by examiner

*Primary Examiner* — Kuen S Lu (74) *Attorney, Agent, or Firm* — K&L Gates LLP (57) ABSTRACT

Computer systems and computer-implemented methods estimate TMB (e.g., computing an "eTMB" value) for a patient based on RNA sequences for the patient.

21 Claims, 5 Drawing Sheets

TOTAL MUTATIONAL BURDEN (TMB) ESTIMATE

PRIORITY CLAIM

The present application claims priority to provisional application Ser. No. 63/117,792, filed Nov. 24, 2020, which is incorporated herein by reference in its entirety.

BACKGROUND

Total mutational burden (TMB) of a cancer genome is the number of somatic mutations (single nucleotide variants and small indels) per megabase of coding regions. Both quantitatively and qualitatively (neoantigen load), various measurements of TMB have shown promise as a predictive biomarker for immune checkpoint inhibitor (ICPI) therapy. Yet variability in assays methodology and in clinical trial results have resulted in confusion about how and when to employ commercialized assays currently available, despite FDA approval of TMB associated with the Foundation One tissue assay and most recently, the blood-based FACT assay. Although efforts are ongoing to harmonize TMB assays, these projects largely focus on standardization of current methodologies rather than improvement of predictive value. ICPI treatment is one of the most expensive cancer therapies (costing over $100,000/year for the payer), can be associated with severe or life-threatening toxicity in the patient, and commonly fails to result in a clinically meaningful tumor response, thereby wasting critical time.

SUMMARY

In one general aspect, the present invention is directed to computer-based systems and methods for computing a TMB-like measure (eTMB) that better focuses on neoantigenic mutations. To that end, embodiments of the present invention can use a probabilistic model to estimate eTMB from RNA-seq. Embodiments of the present invention can, using a new probabilistic model, estimate total mutational burden (TMB) from RNA-seq data, yielding an expression-based TMB estimate (eTMB). The developed probabilistic model will allow for simultaneous modeling of expression levels, prior known variants, variant allele expression frequency, co-mutations, and other-omics data. The model is founded on, but a significant extension of, those currently used for estimating levels of gene and isoform expression that have been developed by the co-inventors. A key advantage of this approach is that it avoids the challenging task of directly calling mutations from RNA-seq data.

In addition, embodiments of the present invention can assess and improve the accuracy and predictive power of eTMB. Using matched whole-exome (WES) and whole transcriptome (RNA-seq) data, under what circumstances (sequencing parameters, cancer types, etc.) eTMB best agrees with the WES-derived TMB can be assessed. The eTMB computation can be refined via a machine learning approach, to optimize its predictive power.

Using a cohort of gastric cancer patients treated with pembrolizumab and for whom WES and RNA-seq data are matched, eTMB's ability to predict efficacy using standard criteria (e.g., RECIST assessment of response [ORR], PFS and OS) can be assessed. Determining all three parameters of efficacy is particularly important for TMB, since a substantial discrepancy is often present between OS versus ORR or PFS. The method can be refined to be a stronger predictor of ICPI benefit and compare the parameters that optimize for agreement with WES-based TMB with those that optimize for tumor response predictive power. Together, these aims will produce the foundation of a more information-rich biomarker.

These and other benefits of the present invention will be apparent from the description that follows.

FIGURES

Various embodiments are described herein in conjunction with the following figures.

DESCRIPTION

Total Mutational Burden (TMB) is an important biomarker for immunotherapy. It is a measurement of the number of somatic mutations (substitutions and small insertions and deletions) within coding regions in the genome of a cancer tumor. For example, TMB has been a variable reported to be an effective, non-overlapping biomarker for efficacy of ICPI monotherapy in squamous cell lung cancer, non-small-cell lung cancer (NSCLC), and other cancers. It is complementary and non-overlapping with other biomarkers such as PD-L1, gene expression signatures, and tumor infiltrating lymphocytes, and is predictive in distinct patient populations. For example, TMB greater than 10 mutations per megabase by the Foundation One assay is reported to predict improved survival in patients with PD-L1 less than 1%. High blood TMB has been associated with atezolizumab efficiency in advanced NSCLC. Of interest, predicted neoantigen load (NAL), postulated to be a more informative subset of TMB, correlates with commercialized TMB measures such as Foundation One's bTMB and GuardantOMNI. Additionally, pembrolizumab has been approved as a second-line treatment for solid tumors in patients with high TMB [greater than or equal to 10 mutations/megabase] and who have no satisfactory alternative treatment options. Despite these positive associates, in some reports, TMB has failed to provide a signal for selecting ICPI patients.

Whether TMB is calculated using whole-genome sequencing (WGS) or whole-exome sequencing (WES) (in research settings) or targeted DNA sequencing panels (in clinical settings), the exact computational definition of TMB varies assay-to-assay (e.g., on whether synonymous mutations are counted and how germline mutations are filtered out), making cross-comparisons difficult, though WES-based and comprehensive genomic profiling-based approaches correlate with each other, and there are efforts to standardize the computation of TMB. Further, although TMB assessment as a continuous variable is informative within a given tumor type, such as NSCLC, assessment as binary variable may be more appropriate in pan-tumor approaches, where major differences in mediate TMB and range are seen between different tumor types. In various embodiments, the present invention focuses on assessment of eTMB as a continuous measure. Also, optimal binarization can be determined.

Central to improving TMB is to focus on neoantigentic mutations rather than gross mutational load. For example, HLA-corrected TMB has shown higher predictive power. An important emerging concept that it is not only the presence or absence of a known neoantigenic mutation but co-mutations such as either p53 or STK11 that alter the impact on ICPI benefit in a major fashion. One aspect of the present invention is that RNA-based TMB-like biomarkers provide a promising route for a measure that better quantifies and integrates neoantigenic mutations and co-mutations.

Genomic TMB computed from DNA has a number of shortcomings, such as: Genomic TMB does not account for mutations that have little effect because they are in genes that are not expressed; Genomic TMB does not account for allele-specific expression; Labeling SNVs as synonymous vs. non-synonymous is difficult with genomic sequencing, especially in genes with complex alternative splicing, frameshifts, and/or indels; Genomic TMB does not make use of expression signatures, leaving an important source of additional information unused; and genomic TMB focusing on coding regions does not account for trans-acting mutations that may affect expression. These deficiencies, coupled with the potential of TMB in several areas, motivates developing a biomarker based on Ribonucleic acid (RNA) sequencing—either using whole transcriptome sequencing (WTS) or targeted RNA panels.

Figure 1:
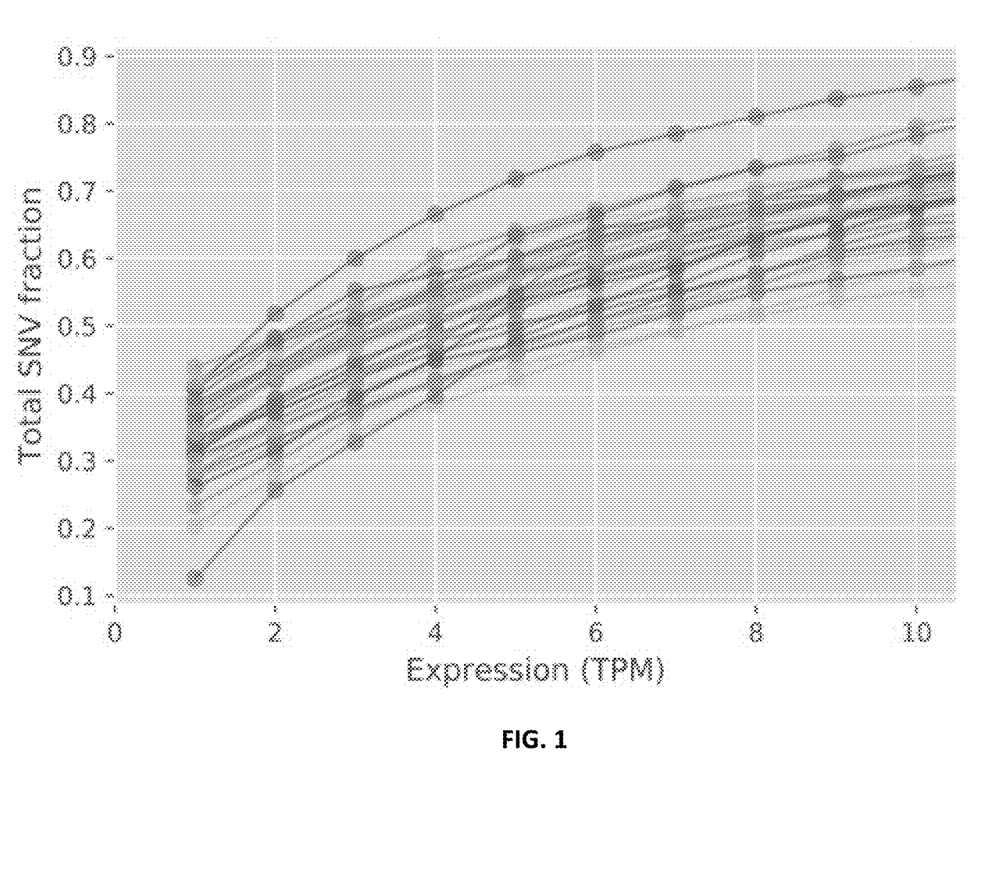
FIG. 1 is a graph that shows a distribution of number of WES-called SNVs occurring in genes of low expression. Each curve represents a gastric tumor sample. Point (x, y) plots the fraction of SNVs (y) in genes with expression <x TPM.

By using RNA sequencing, (1) mutations can be weighted based on the expression of the gene they are in; (2) differential effects of mutations in each allele can be modeled; (3) synonymous mutations can be more easily filtered (or weighted appropriately); (4) frameshift indels, which are associated with immunogenicity, are more readily detectable; (5) the estimated mutational load can be combined with expression patterns, creating a richer source of predictive features; and (6) even mutations that are outside of the sequenced mRNA (i.e. in a promoter or transcription factor binding site) can be indirectly observed via their effect on gene expression. FIG. 1 shows in a representative data set that between 12% and 43% of WES-called SNVs occur in genes that are expressed at less than or equal to 1 transcript per million (TPM)—a level of expression that would often be filtered out in downstream analyses.

In addition, computing TMB from RNA has a higher potential for deriving more information-rich and specific biomarkers because coupled expression estimates and related features (such as splicing information, novel isoforms, etc.) are naturally available. For example, it is possible from RNA-seq data to correlate TMB with expression estimates for particular genes and isoforms. It will eliminate of some sources of variability as a confounding factor: since both expression and eTMB would be derived from the same set of sequencing reads, variability introduced by sample preparation, separate biopsies, and sequencing randomness is eliminated.

These attributes of eTMB have the potential to refine what is currently a very gross-scale TMB into a family of RNA-derived immunoreactive signatures that are targeted to particular cancer types or treatments.

One aspect of the present invention is the use of an existing and widely-used sequencing assay (RNA-seq) for a novel purpose (TMB inference), supplementing or replacing an assay based on DNA. This will facilitate several additional downstream innovations, including relating expression of specific genes or pathways with mutational burden and development of predictors with improved accuracy using the additional signal that expression brings.

In one aspect, the present invention is methodologically innovative since it avoids directly calling mutations using RNA-seq—a challenging task in itself. The proposed approach is instead based around a probabilistic model with TMB used as a parameter for a prior distribution. The eTMB is then learned by fitting the probabilistic model to the observed data. The advantage of this approach is that (1) it avoids the need to call variants directly; (2) it avoids setting arbitrary thresholds for variant's presence or absence; (3) it allows for joint modeling of sequencing biases (GC content, sequence-specific, position) and the TMB, allowing the inference of TMB to account for non-uniform RNA-seq coverage; (4) it allows for estimating confidence intervals of the eTMB measure rather than a point estimate; and (5) it incorporates prior knowledge (germline variants) and other-omics data (i.e. paired WES or paired normal) within the same framework.

The main challenge in computing the TMB from RNA-seq is that it has traditionally been difficult to accurately call single nucleotide variants (SNVs) and small indels reliably from RNA-seq data. This is due to the confounding factors of sequencing biases introducing non-uniform coverage as well as the varied levels of expression of genes and their isoforms. Hence, the straightforward approach to computing TMB with RNA that first identifies mutations and then counts them is not likely to be successful, leading to a computational modeling challenge.

Embodiments of the present invention provide an approach to solving this problem that avoids the step of calling individual mutations from the RNA-seq data. Rather, the present invention can use, in various embodiments, a probabilistic model of generated RNA-seq reads that takes the TMB $\theta$ as a parameter. This probabilistic model $M(\theta)$ will also account for common RNA-seq sequencing biases such as sequence-specific, fragment-GC content, and positional biases. It will also account for known germline mutations using databases of common variants. Available gene expression quantification software can be used to optimize a comprehensive model of RNA-seq biases, which can be leveraged in this work. Given this model M (designed and refined through parameter fitting), an algorithm can be defined to find:

$$eTMB := \underset{\theta}{\mathrm{argmax}}\, Pr(\text{observed } RNA-seq \text{ reads}|M(\theta)). \quad (1)$$

This is the TMB value $\theta^*$ that maximizes the probability of observing the given reads under a model that assumes the TMB is $\theta^*$. Hence, this approach sidesteps the difficult issue of selecting individual mutations and instead finds the parameters (including the eTMB) that maximizes the data likelihood. In addition, rather than encode important filtering or correction steps in ad hoc data manipulation steps, the probabilistic model can account for these corrections in a uniform model.

Next described is how to, according to various embodiments, design, implement, and refine a probabilistic model that will estimate eTMB from RNA-seq samples. The approach, in various embodiments, can build atop the well-established probabilistic models used for transcript quantification and augment them with the capability to estimate the total mutational burden present in the sample. The generative model for RNA-seq data posits that the likelihood $L(\alpha)$ of the vector $\alpha$ of the relative abundances of each transcript is:

$$L(\alpha) = \Pi_{f \in F} \Sigma_{a_{f,t,i} \in aln(f)} Pr(t|\alpha) Pr(a_{f,t,i}|t) \qquad (2)$$

where F is the set of sequenced fragments and $a_{f,t,i} \in aln(f)$ are the set of transcripts and positions where sequenced fragment f has aligned. This likelihood is conditioned on the sequences of the set T of known transcripts. These sequences determine the alignments that will be made and dictate the conditional probabilities $Pr(a_{f,t,i}|t)$, for observing fragment f arising from position i of transcript t under the alignment $a_{f,t,i}$.

Avoid calling mutations. An extended model can be used such that, instead of being a fixed transcriptome, T will be a sequence model that can be updated given the observed reads. Specifically, assume that, using a standard optimization procedure such as the variational Bayesian expectation maximization (VBEM) algorithm, a maximum likelihood estimate (e.g. a summary statistic) of the relative transcript abundances $\alpha^*$ can be obtained. This allows a posterior probability model to be inferred or sampled from the probabilistic model given the observed data. For example, a posterior probability $Pr(a_{f,t,i}|\alpha^*)$ can be assigned to each alignment of each read. In such an embodiment, the eTMB value can a summary statistic or set of summary statistics (e.g., maximum likelihood estimates) of the posterior probability distribution.

Advantageously, various embodiments of the present invention can use this posterior probability to estimate the likelihood of each mutation implied by the reads aligning to the transcripts. Specifically, consider a single locus i on a particular transcript t with a known reference nucleotide $r[t_i]$ (i.e. $r[t_i]$ is the nucleotide at position i of transcript t). The goal is to estimate $Pr(s[t_i] \neq r[t_i])$, the probability that position i of transcript t within the sample s is not equal to the reference sequence of transcript t at position i. This probability can be estimated as:

$$Pr(s[t_i] \neq r[t_i]) = \frac{\sum_{a_{f,t,j} \neq t_i} Pr(a_{f,t,j}|\alpha^*)}{\sum_{a_{f,t,j} \cong t_i} Pr(a_{f,t,j}|\alpha^*)} \qquad (3)$$

where $a_{f,t,i} \neq t_i$ denotes an alignment overlapping t; where the aligned base at $t_i$ does not agree with $r[t_i]$ and $a_{f,t,i} \cong t_i$ is the set of all alignments overlapping $t_i$. This framework leads to an iterative algorithm in which it is possible to solve the likelihood problem posed by Equation (2), and then subsequently re-estimate the mutation probabilities using Equation (3); a process that can be repeated until the estimates of Equation (3) converge.

Given the converged estimates of the mutation probabilities, the eTMB can be computed by integrating the mutation probabilities over all positions of all transcripts. That is:

$$\theta^* = \sum_{t \in T} \sum_{i=1}^{|t|} Pr\bigl(s[t_i] \neq r[t_i]\bigr) / \sum_{t \in T} |t|.$$

This is an estimate of the total fraction of mutated nucleotides in the transcriptome (the eTMB $\theta^*$).

To better focus on mutations that effect neoantigen load, Equation (3) can be augmented to: (1) incorporate priors and adjustments to the probabilities using databases of common SNV (single nucleotide variant) frequencies to filter out germline mutations; (2) model indels (the above discussion describes only SNVs for simplicity of exposition); (3) model non-uniform variant allele expression frequency; (4) model synonymous vs. non-synonymous mutations; (5) include WES and other omics signals; (6) include terms for known co-mutations. By, for example, bootstrapping the reads observed in the sequencing the experiment and re-performing the estimation, both an estimate of the eTMB can be derived, along with an assessment in the confidence in this estimate (i.e. a confidence interval or credible interval—depending on the posterior estimation method—can be provided). The procedure may be performed repeatedly or iteratively until some termination criterion is met (e.g., the change in the confidence measure is less than a threshold value). This could also be done by appropriately sampling from the posterior distribution using a technique such as MCMC (Markov chain Monte Carlo) or other efficient Monte Carlo sampling techniques such as Hamiltonian Monte Carlo (HMC) sampling, No U-Turn Sampling (NUTS), Gibbs sampling, or similar or related approaches, or heuristic optimization algorithms such as genetic algorithms, or simulated annealing. Thus, eTMB can be treated as a continuous variable with credible intervals.

In various implementations, if an EM (expectation-maximization) optimization approach cannot be constructed to fit the model, alternative optimization approaches can be used such as MCMC (Markov chain Monte Carlo), genetic algorithms, and simulated annealing. If the probabilistic model does not correlate well with the ground truth, the alternative approach of explicitly calling mutations from RNA-seq data (developing a new approach for this by re-purposing some of the developed model to account for non-uniform RNA-seq coverage) can be used; or an assembly-based approach can be used.

The probabilistic model proposed above is really a family of models defined by several parameters. Using, for example, the validation sets below, the probabilistic model and optimization approaches can be improved to improve the correlation between WES-derived TMB and eTMB and to improve its predictive power. To do this, additional parameters can be introduced into the model M and the WES/RNA-seq pairs and tumor response can be used as training data to learn an improved model. $M(\theta)$ can be reparametrized to be $M(\theta; \vec{v})$ where $\vec{v}$ is a set of weights for various parts of the model. Then, $M(\bullet; \vec{v})$ can be optimized to maximize accuracy of the eTMB value for predicting response to immunotherapy over a set of patients, such as by minimizing the disagreement between eTMB and WES-based TMB or by maximizing predictive accuracy for various endpoints. Here, $\vec{v}$ can encode which genes or pathways are included in the computation, weights for various sequencing bias terms, which sources of germline mutations are given higher weight, etc. By optimizing v, the eTMB approaches that have the highest utility can be selected for the family of eTMB approaches.

The set of weights can model the contribution of each human gene transcript to the computation of the eTMB value. The set of weights could also model the contribution of each human genetic locus (taken as a, possibly transformed, aggregation of the transcript contributions) to the computation of the eTMB value. The set of weights can also model the contribution of each biological pathway (as composed by the appropriate aggregation of its constituent gene transcripts) to the computation of the eTMB value. The set of weights and their values may also be optimized by manual tuning based on, for example, prior biological expertise.

A variant of the eTMB would estimate the TMB on a subset of genes, selected based on one or more of the following factors, among others: (1) improved predictive power, (2) improved correlation with WES-based eTMB, (3) prior knowledge of cancer-related genes, (4) estimates of gene expression values, (5) known biological function and pathways. This targeted eTMB may be put to the same or expanded uses compared with the whole-genome eTMB. A subset of genes, transcripts, or genomic regions for inclusion within the eTMB predictor or targeted eTMB predictor can be chosen via optimization or machine learning methods, by, for example, again reparametrizing the model to include variables indicating whether the given gene, transcript, or genomic region (or set thereof) is to be included in the eTMB computation. Values for these variables can be set to optimize predictive power, loss, accuracy, or data likelihood using several optimization techniques. Another variant of the eTMB introduces arbitrary weighting on the genes, transcripts, genomic regions, pathways or subsets of those items. These arbitrary weights can be selected via various machine learning or optimization techniques to optimize predictive power, accuracy, or other desired features.

The eTMB in each of its various forms can be optimized, parameterized, and applied separately to varied cancer types and subtypes. For example, using a training data of lung cancer samples, the eTMB can be refined and optimized for predictive power in that disease. Such parameterization may be different than, for example, that optimized for gastric cancer. Each disease-specific eTMB is a particular implementation or instantiation of the eTMB framework described here. Similarly, the eTMB can be parameterized to predict efficacy of various treatment regimens, yielding a family of predictive values for different treatments.

Additional biomarkers that combine eTMB, expression signatures, metadata, clinical variables, or other molecular features can be developed, or eTMB in its various versions can be integrated into larger predictive systems as one of several informative features.

eTMB, in several of its various forms, can be computed on a patient's data to derive eTMB values obtained from the various forms. These eTMB values can be augmented with molecular features, as well as clinical measurements, patient demographics, and other biomarkers to produce "eTMB signatures." Molecular features that can be integrated with eTMB include (1) structural variants and gene fusions, (2) percent spliced in and alternative splicing events, and (3) gene and transcript expression values. These eTMB signatures that include both various eTMB values and other patient measurements can be used to train predictors for response to immunotherapy. Training of the predictors can be achieved through various machine learning training algorithms. Examples of machine learning training algorithms include Support Vector Machines, Random Forests, Neural Networks, probabilistic graphical models, and logistic regression.

Figure 4:
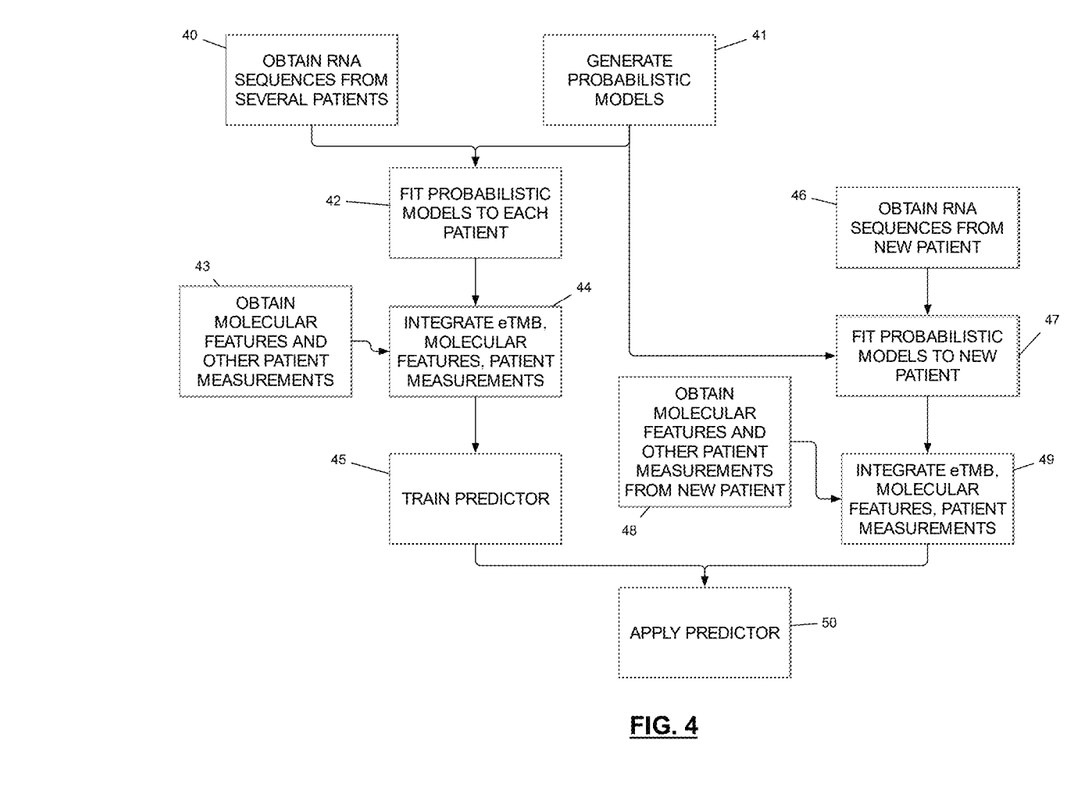
FIG. 4 is a flow chart of a process according to other various embodiments of the present invention.

FIG. 4 is a flow chart of a process according to various embodiments of the present invention as (optionally) integrated with various additional modalities of omics data and applied in the context of training, validating and applying the estimates of the model as a predictor. The systems shown in FIG. 2 and/or FIG. 5 can be used to perform steps of the method shown in FIG. 4. At step 40, RNA sequences from several patients are obtained and step 41 the probabilistic models are generated as described herein. Then at step 42 the probabilistic models can be fit to each patient from which RNA sequences were obtained at step 40. This can yield the eTMB values for the patients as described herein. Also, at step 42, molecular features and other measurements from the patients are obtained so that, at step 44, the eTMB values for the patients can be integrated with the molecular features and other measurements of the patients (e.g., collectively, eTMB signatures for the patients). The integrated eTMB values, molecular features and patient measurements can then be used to train the predictors at step 45 as described above.

The right side of FIG. 4 pertains to applying the predictor trained at step 45 to a new patient. At step 46, the RNA sequences of the new patient are obtained. At step 47, the probabilistic models generated at step 41 are fit to the new patient's RNA sequences to yield the eTMB values for the new patient. At step 48, other data for the new patient are captured, such as molecular features and other patient measurements, which are integrated at step 49 with the eTMB values computed at step 47 to generated the eTMB signature for the new patient, so that, at step 50, the eTMB signature can be applied to the predictor trained at step 45 to predict the new patient's response to immunotherapy.

As temporal patterns of gene and transcript expression have been demonstrated as useful in many existing biological analyses, the invention described herein can also be adapted to account for time-varying eTMB patterns, either over the entire transcriptome, or over specific (potentially time-varying) subsets of genes or transcripts. As different subsets of genes may yield the most prognostic power at different diseases stages and states, the RNA-seq-based eTMB measure can be assumed to encompass modifications that compute not only the estimate of the TMB, but also the dynamic TMB signatures and the relevant sets of genes that provide the most clinical utility.

Treating eTMB as a continuous variable, two validation approaches can be used, for example. First is concordance with WES TMB. Using the data sets in Table 1 or other similar data sets, TMB can be computed from WES data to provide a set of WES-derived TMB values, by implementing several variations of existing TMB pipelines, to obtain several estimates of the WES-based TMB. These pipelines vary in how they filter suspected germline mutations (using, e.g., dbSNP, 1000 Genomes, or other lists of common variants), in how they call SNVs, and which regions of the genome they consider. The RNA-seq-based eTMB approach described herein can be considered with the WES-based TMB estimates. Agreement across various slices of the samples can be considered, including per cancer type, per coverage depth (varied by subsampling reads randomly), estimated sequencing bias patterns, and stratified by WES-based TMB. This will provide a comprehensive picture of the level of agreement between WES-based TMB and eTMB in various scenarios.

TABLE 1

Data sets in hand for initial assessment of eTMB

| Name | WES | RNA-seq | n | Description |
|---|---|---|---|---|
| Gastric Cancer | ✓ | ✓ | 55+ | Matched tumor-normal WES/RNA-seq patients who received pembrolizumab as a $2^{nd}$-or $3^{rd}$-line treatment |
| TCGA | ✓ | ✓ | 10,000 | The Cancer Genome Atlas (TCGA) samples across a range of cancers with both RNA-seq and WES or WGS |
| Lung Squamos Cell Carcinoma | ✓ | ✓ | 101 | Data set from Seo et al. |

Figure 2:
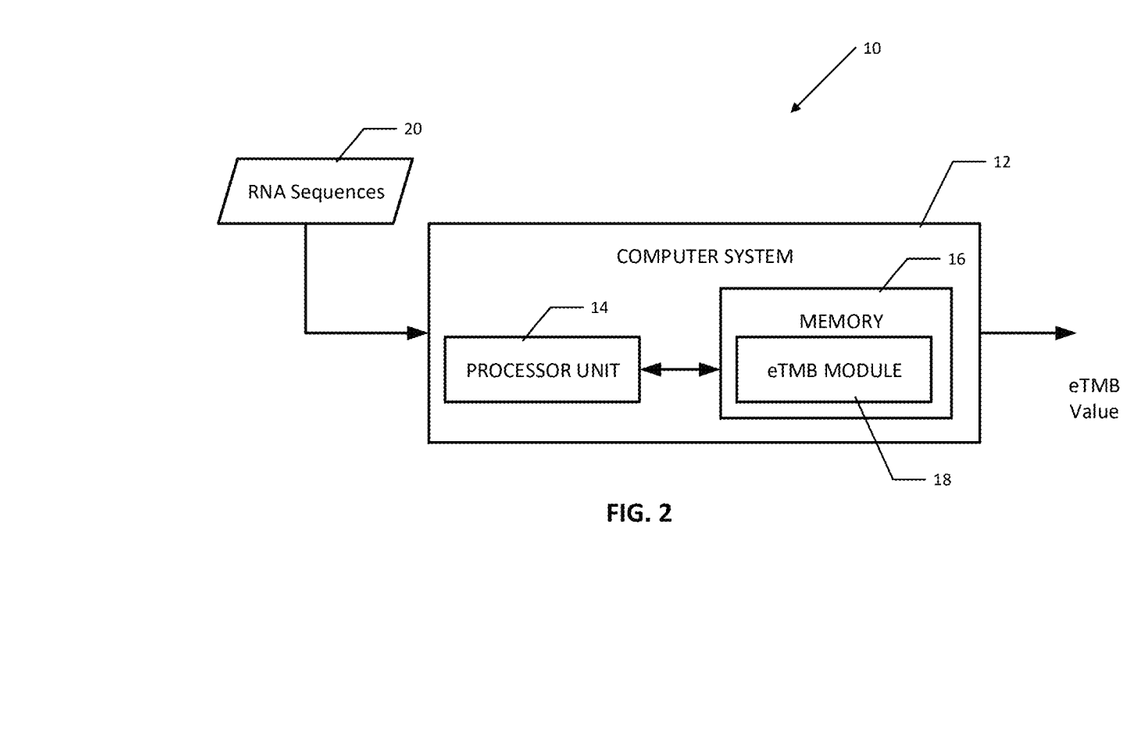
FIG. 2 is a diagram of an operational system using the probabilistic model for generating the eTMB estimate according to various embodiments of the present invention.

FIG. 2 is a diagram of an operational system 10 using the probabilistic model for generating the eTMB estimate according to various embodiments. The system can be used to perform steps of the method shown in FIG. 3, described below. As shown in FIG. 2, the operational system comprises a computer system 12 that comprises one or more processor units 14 and one or more memories 16. For convenience, only one of each is shown in FIG. 2. Each processor unit 14 may comprise one or more processor cores. The memory 16 stores a software module, e.g., the "eTMB Module" 18, that implements the trained and optimized probabilistic model for generating the eTMB value as described above. The processor core(s) 14 execute the software module 18, which causes the processor core(s) 14 to compute the eTMB value based on the input RNA sequences 20 for the patient. The RNA sequences (and WES/WGS data if used) can be input to the computer system via data files, such as FASTQ or FASTA data files.

Each processor unit may comprise on-board memory (ROM or RAM) (not shown) and off-board memory. The on-board memory may comprise primary, volatile and/or non-volatile, storage (e.g., storage directly accessible by the processor cores). The off-board memory may comprise secondary, non-volatile storage (e.g., storage that is not directly accessible by the processor cores), such as ROM, HDDs, SSD, flash, etc. The processor cores may be CPU cores, GPU cores and/or AI accelerator cores. GPU cores operate in parallel (e.g., a general-purpose GPU (GPGPU) pipeline) and, hence, can typically process data more efficiently than a collection of CPU cores, but all the cores of a GPU execute the same code at one time. AI accelerators are a class of microprocessor designed to accelerate artificial neural networks. They typically are employed as a co-processor in a device with a host CPU as well. An AI accelerator typically has tens of thousands of matrix multiplier units that operate at lower precision than a CPU core, such as 8-bit precision in an AI accelerator versus 64-bit precision in a CPU core.

In embodiments where there are multiple processor units, the processor units could be co-located or distributed. For example, the processor units may be interconnected by data networks, such as a LAN, WAN, the Internet, etc., using suitable wired and/or wireless data communication links. Data may be shared between the various processing units using suitable data links, such as data buses (preferably high-speed data buses) or network links (e.g., Ethernet).

The software for the various computer systems described herein and other computer functions described herein may be implemented in computer software using any suitable computer programming language such as .NET, C, C++, Rust, Go, Java, *Julia*, Nim, Python, Scala, Seq, or Zig using conventional, functional, or object-oriented techniques. Programming languages for computer software and other computer-implemented instructions may be translated into machine language by a compiler or an assembler before execution and/or may be translated directly at run time by an interpreter or virtual machine. Examples of assembly languages include ARM, MIPS, and x86; examples of high level languages include Ada, BASIC, C, C++, C#, COBOL, CUDA, Fortran, Java, Lisp, Pascal, Go, Rust, Object Pascal, Haskell, ML, Seq; and examples of scripting languages include Bourne script, JavaScript, *Julia*, Python, Ruby, Lua, PHP, and Perl.

Figure 3:
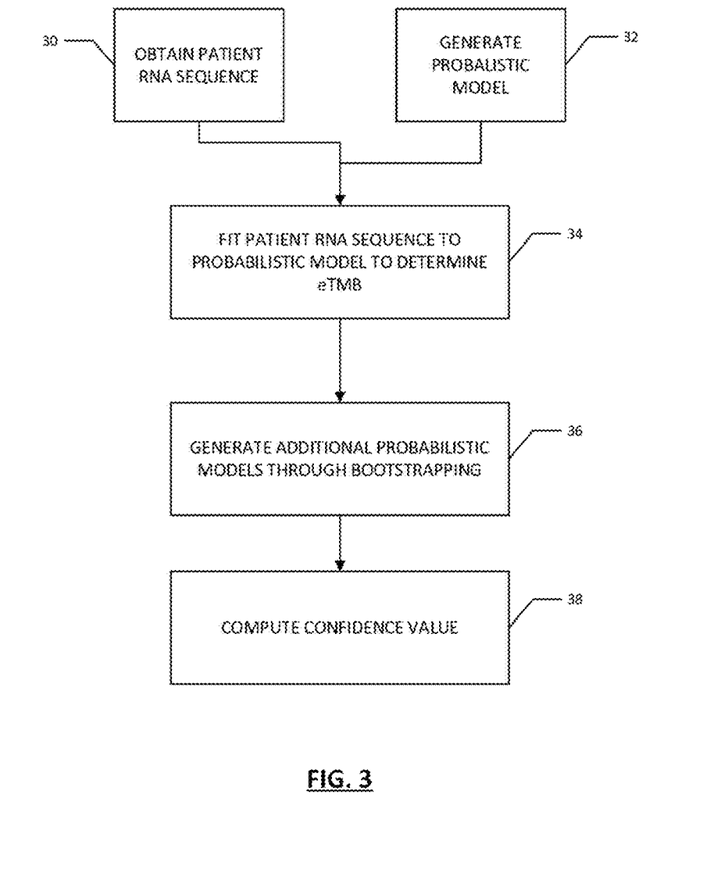
FIG. 3 is a flow chart of a process according to various embodiments of the present invention.

FIG. 3 is a flow chart of a process according to various embodiments of the present invention. At step 30, the RNA sequence for the patient for whom the eTMB value is being calculated is obtained. Tumor tissue can be isolated from a human patient during a biopsy procedure or surgery. All tumor tissue specimens can be collected in frozen and fresh conditions and transferred by nitrogen tank from a surgery/biopsy room directly to a laboratory for preparation. Diethylpyruvate carbonate (DEPC) can be used for removing RNase for all surgery sets. For RNA extraction from the tumor tissue specimen, first, liquid nitrogen can be added to the tumor tissue sample and the tumor tissue can be ground to a powder. Next, either Trizol reagent (Invitrogen, USA) or TriPure (Roche, USA), for example, can be added. Upon completion of the harvest procedure, the homogenate can be transferred to an empty RNase free falcon tube stored on ice. To prevent microbial contamination and subsequent RNase contamination, disposable gloves are preferably used and good sterile technique and methods are preferably practiced when handling the sample. Ethanol (250 µl), isopropanol (500 µl), and chloroform (200 µl) can be added respectively. β-mercaptoethanol can then be added to the homogenate to remove any RNase. The final RNA sample can then sent to a sequence facility for RNA sequencing. The RNA sequencing data can be stored in data files, such as FASTQ or FASTA data files.

At step 32 (which can be performed before, after, or simultaneously with step 30), the probabilistic model can be generated as described above. Then, at step 34, the patient's RNA sequence can be fit to the probabilistic model as described above to compute the eTMB value for the patient. At step 36, one or more additional probabilistic models can be generated using bootstrapping as described above (or a posterior distribution can be inferred using Bayesian inference techniques as described above) such that, at step 38, a confidence measure for the computed eTMB can be determined. The eTMB value can be a biomarker for immunotherapy as described above. For example, if the patient's eTMB value is greater than a minimum threshold value, immune checkpoint inhibitor (ICPI) therapy can be administered to the patient. The probabilistic model can also be optimized to maximize the accuracy of the eTMB value for predicting response to immunotherapy over a set of patients.

As described above, the probabilistic model can be tailored to, for example, certain types of cancers or other diseases. For example, if the patient's specimen is a lung tumor specimen, the probabilistic model can be trained with RNA sequences from subjects with lung cancer; if the patient's specimen is a gastric tumor specimen, the probabilistic model can be trained with RNA sequences from subjects with gastric cancer; and so on for different types and sub-types of cancers or other diseases.

In various aspects, therefore, the eTMB value for a patient can be derived from the RNA-sequence data for the patient. In one approach, as described above, a statistical approach, such a maximum likelihood, which can be obtained using a computational procedure like an expectation maximization (EM) algorithm, can be used to find parameters of the probabilistic model that maximizes the likelihood of the observed data (e.g., the patient's RNA sequence). The probabilistic model can comprise a set of weights, such that computing the eTMB value can comprise optimizing the set of weight to maximize accuracy of the eTMB value for predicting response to immunotherapy over a set of patients. The set of weights can model the contribution of each human gene transcript to the computation of the eTMB value. The set of weights could also model the contribution of each human genetic locus (taken as a, possibly transformed, aggregation of the transcript contributions) to the computation of the eTMB value. The set of weights could also model the contribution of each biological pathway (as composed by the appropriate aggregation of its constituent gene transcripts) to the computation of the eTMB value. Also, the set of weights could be optimized by manual tuning, based on prior biological expertise. The optimization approach can be coupled with a procedure, like bootstrapping as described above, to estimate the variance of the point estimate.

Another approach is to sample from the posterior distribution of the probabilistic model parameters given the data as the observations. Rather than finding the model parameters that "maximize" the data likelihood, the output of such a sampling approach is an entire distribution over the parameters, and assigning each value the parameter can take some approximate probability. Such sampling-based approaches are often much more computationally intensive, but they yield distributions as output which can then be summarized (e.g., a summary statistic, such as taking the mode as the most likely point, looking at the credible interval to decide how likely the true parameter is in some range, etc.) and they therefore also tend to be more robust.

In one general aspect, therefore, the present invention is directed to computer systems and computer-implemented methods for estimating expression-based TMB (e.g., computing an "eTMB" value) for a patient based on RNA sequences for the patient. A method, according to various embodiments, comprise generating, by a programmed processor, a probabilistic model from RNA sequence reads from an RNA sequence dataset, where total mutational burden (TMB) is a parameter of a prior distribution of the RNA sequence dataset, such that the probabilistic model has a TMB parameter. The method also comprises the steps of obtaining a patient RNA sequence data for a patient; and computing, by the programmed processor, an eTMB value for the patient using the probabilistic model and based on the patient RNA sequence data.

In various implementations, computing the eTMB value comprises fitting, by the programmed processor, the probabilistic model to the patient RNA sequence data, where fitting the probabilistic model to the patient RNA sequence data comprises computing an eTMB value for the patient, where the eTMB value is computed as a value that maximizes a probability of observing the RNA sequence reads of the probabilistic model, assuming that the TMB parameter for the probabilistic model is the eTMB value.

In various implementations, computing the eTMB value comprises computing, by the programmed processor, a summary statistic of a posterior probability distribution derived from the probabilistic model given the patient RNA sequence data.

In various implementations, the eTMB value is a predictive biomarker for immunotherapy for the patient; and the method further comprises administering immunotherapy to the patient upon a determination that the eTMB value for the patient meets or exceeds a threshold value. For example, the eTMB value can be a predictive biomarker for immune checkpoint inhibitor (ICPI) therapy for the patient, in which case administering immunotherapy can comprise immune checkpoint inhibitor (ICPI) therapy to the patient.

In various implementations, the RNA sequence dataset is from subjects having a first disease, such that the probabilistic model is trained to be specific to the first disease. The first disease can be a form of cancer.

In various implementations, the probabilistic model is optimized to minimize disagreement between the eTMB value and a whole-exome-sequencing (WES)-based TMB value for the patient. The probabilistic model can also be optimized to maximize an accuracy of the eTMB value for predicting response to immunotherapy over a set of patients.

In various implementations, the RNA sequence reads comprise parts of transcripts; and the eTMB value is computed by integrating mutation probabilities over all positions of all transcripts of the RNA sequence reads.

In various implementations, the eTMB value is an estimate of mutated nucleotides in a transcriptome of the patient RNA sequence data. The probabilistic model can also filter out germline mutations by using databases of common SNP frequencies. The probabilistic model can also model non-uniform variant allele expression frequency.

In various implementations, the method further comprises computing, by the programmed processor, a confidence estimate for the computed eTMB value.

In various implementations, generating the probabilistic model comprises generating a first probabilistic model; and computing the confidence estimate comprises, repeatedly until a stopping criterion is met: (i) generating an additional probabilistic model by bootstrapping the RNA sequence reads used in the first probabilistic model; and (ii) recomputing the eTMB value with the additional probabilistic model.

In various implementations, fitting the probabilistic model to the patient RNA sequence data comprises employing an expectation-maximization optimization algorithm. The probabilistic model can comprise a set of weights, and computing the eTMB value can comprise optimizing the set of weights to maximize accuracy of the eTMB value for predicting response to immunotherapy over a set of patients. The set of weights models a contribution of each human gene transcript to the computation of the eTMB value.

In another general aspect, a method according to various embodiments of the present invention comprises the step of computing, for each patient in a cohort, by a programmed processor, an eTMB value according to the techniques described herein, where the eTMB value is a predictive biomarker for immunotherapy for the patient. The method also comprises the step of combining, by the programmed processor, a vector of eTMB values for the patients in the cohort with one or more other biomarkers and/or one or more molecular measurements for the patients in the cohort to obtain an eTMB signature for each patient. The method also comprises the step of training, by the programmed processor, a function that estimates a likelihood of response to immunotherapy, where training the function comprises applying a machine learning training method to the eTMB signatures. The method also comprises the steps of, after training the function, for a new patient: (i) computing, by the programmed processor, an eTMB value for the new patient as described herein; (ii) obtaining one or more biomarkers and/or one or more molecular measurements for the new patient to obtain an eTMB signature for the new patient; and (iii) applying, by the programmed processor, the trained function to the eTMB signature of the new patient to estimate a patient likelihood of response to immunotherapy for the new patient.

In various implementations, the patient likelihood is a predictive biomarker for immunotherapy for the patient; and the method further comprises administering immunotherapy to the patient upon a determination that the patient likelihood of response to immunotherapy for the new patient meets or exceeds a threshold value. The patient likelihood can be a predictive biomarker for immune checkpoint inhibitor (ICPI) therapy for the new patient, such that administering immunotherapy comprises administering ICPI therapy to the new patient upon a determination that the predictive biomarker for ICPI therapy for the new patient meets or exceeds a threshold value.

In another general aspect, the present invention is directed to a computer system comprising a processor core and a memory. The memory stores software that, when executed by the processor core, cause the processor core to: generate a probabilistic model from RNA sequence reads from an RNA sequencing dataset, where total mutational burden (TMB) is a parameter of a prior distribution of the RNA sequence dataset, such that the probabilistic model has a TMB parameter; and compute an eTMB value for a patient based on a patient RNA sequence obtained from the patient and using the probabilistic model.

In various implementations, the software, when executed by the processor core, causes the processor core to compute the eTMB value by fitting the probabilistic model to the patient RNA sequence, where the eTMB value is computed as a value that maximizes a probability of observing the RNA sequence reads of the probabilistic model, assuming that the TMB parameter for the probabilistic model is the eTMB value.

In various implementations, the software, when executed by the processor core, causes the processor core to compute the eTMB value by computing a summary statistic of a posterior probability distribution derived from the probabilistic model given the patient RNA sequence.

In another general aspect, the memory stores software that, when executed by the processor core, cause the processor core to: (i) compute, for each patient in a cohort, an eTMB value, as described herein; (ii) combine a vector of eTMB values for the patients in the cohort with one or more other biomarkers and/or one or more molecular measurements for the patients in the cohort to obtain an eTMB signature for each patient; (iii) train a function that estimates a likelihood of response to immunotherapy by applying a machine learning training method to the eTMB signatures; and, after training the function, for a new patient: (iv) compute an eTMB value for the new patient by using the probabilistic model and based on a patient RNA sequence obtained from the new patient; and (v) apply the trained function to the eTMB signature of the new patient to estimate a patient likelihood of response to immunotherapy for the new patient, where the eTMB signature is obtained by combining one or more biomarkers and/or one or more molecular measurements for the new patient with the eTMB value for the new patient.

Figure 5:
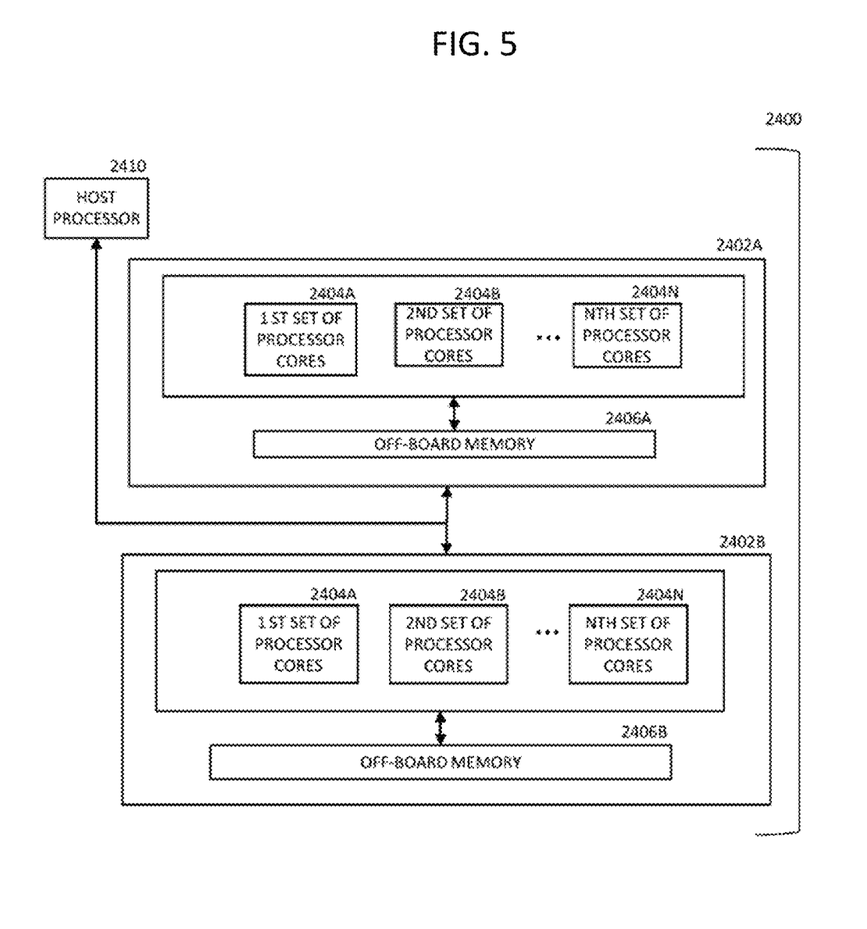
FIG. 5 is a diagram of a computer system according to various embodiments of the present invention.

FIG. 5 is a diagram of a computer system 2400 that could be used to implement the embodiments described above, such as the methods shown in FIGS. 3 and 4. The illustrated computer system 2400 comprises multiple processor units 2402A-B that each comprises, in the illustrated embodiment, multiple (N) sets of processor cores 2404A-N. Each processor unit 2402A-B may comprise on-board memory (ROM or RAM) (not shown) and off-board memory 2406A-B. The on-board memory may comprise primary, volatile and/or non-volatile storage (e.g., storage directly accessible by the processor cores 2404A-N). The off-board memory 2406A-B may comprise secondary, non-volatile storage (e.g., storage that is not directly accessible by the processor cores 2404A-N), such as ROM, HDDs, SSD, flash, etc. The processor cores 2404A-N may be CPU cores, GPU cores and/or AI accelerator cores. GPU cores operate in parallel (e.g., a general-purpose GPU (GPGPU) pipeline) and, hence, can typically process data more efficiently that a collection of CPU cores, but all the cores of a GPU execute the same code at one time. AI accelerators are a class of microprocessor designed to accelerate artificial neural networks. They typically are employed as a co-processor in a device with a host CPU 2410 as well. An AI accelerator typically has tens of thousands of matrix multiplier units that operate at lower precision than a CPU core, such as 8-bit precision in an AI accelerator versus 64-bit precision in a CPU core.

In various embodiments, the different processor cores 2404 may train and/or implement different networks or subnetworks or components. For example, in one embodiment, the cores of the first processor unit 2402A may implement the eTMB module 18 of FIG. 2. As another example, with reference to FIG. 4, the cores of the first processor unit 2402A may fit the probabilistic models to patients at steps 42 and 47, and the cores of the second processing unit 2402B may train and apply the predictors at steps 45 and 50. One or more host processors 2410 may coordinate and control the processor units 2402A-B.

In other embodiments, the system 2400 could be implemented with one processor unit 2402. In embodiments where there are multiple processor units, the processor units could be co-located or distributed. For example, the processor units 2402 may be interconnected by data networks, such as a LAN, WAN, the Internet, etc., using suitable wired and/or wireless data communication links. Data may be shared between the various processing units 2402 using suitable data links, such as data buses (preferably high-speed data buses) or network links (e.g., Ethernet).

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. Further, it is to be understood that the figures and descriptions of the present invention have been simplified to illustrate elements that are relevant for a clear understanding of the present invention, while eliminating, for purposes of clarity, other elements. While various embodiments have been described herein, it should be apparent that various modifications, alterations, and adaptations to those embodiments may occur to persons skilled in the art with attainment of at least some of the advantages.

The disclosed embodiments are therefore intended to include all such modifications, alterations, and adaptations without departing from the scope of the embodiments as set forth herein.

What is claimed is:

1. A method comprising:
computing, for each patient in a cohort, by a programmed processor, a total mutational burden (TMB) estimate (eTMB) value,
wherein the eTMB value is a predictive biomarker for immunotherapy for the patient, and
wherein computing the eTMB values comprises:
generating, by the programmed processor, a probabilistic model from Ribonucleic acid (RNA) sequence reads from an RNA sequence dataset,
where the TMB is a parameter of a prior distribution of the RNA sequence dataset, such that the probabilistic model has a TMB parameter; and
for each patient in the cohort:
obtaining a patient RNA sequence data for a patient;
computing, by the programmed processor, an eTMB value for the patient using the probabilistic model and based on the patient RNA sequence data;
combining, by the programmed processor, a vector of eTMB values for the patients in the cohort with one or more other biomarkers and/or one or more molecular measurements for the patients in the cohort to obtain an eTMB signature for each patient;
training, by the programmed processor, a function that estimates a likelihood of response to immunotherapy,
wherein training the function comprises applying a machine learning training method to the eTMB signatures; and
after training the function, for a new patient:
computing, by the programmed processor, an eTMB value for the new patient,
wherein computing the eTMB values comprises:
obtaining a patient RNA sequence data for the new patient;
computing, by the programmed processor, an eTMB value for the new patient using the probabilistic model and based on the patient RNA sequence data for the new patient;
obtaining one or more biomarkers and/or one or more molecular measurements for the new patient to obtain an eTMB signature for the new patient; and
applying, by the programmed processor, the trained function to the eTMB signature of the new patient to estimate a patient likelihood of response to immunotherapy for the new patient.

2. The method of claim 1, wherein:
the patient likelihood is a predictive biomarker for immunotherapy for the patient; and
the method further comprises administering immunotherapy to the patient upon a determination that the patient likelihood of response to immunotherapy for the new patient meets or exceeds a threshold value.

3. The method of claim 2, wherein:
the patient likelihood is a predictive biomarker for immune checkpoint inhibitor (ICPI) therapy for the new patient; and
administering immunotherapy comprises administering ICPI therapy to the new patient upon a determination that the predictive biomarker for ICPI therapy for the new patient meets or exceeds a threshold value.

4. A computer system comprising:
a processor core; and
a memory that stores software that, when executed by the processor core, cause the processor core to:
compute, for each patient in a cohort, a total mutational burden (TMB) estimate (eTMB) value, wherein the eTMB value is a predictive biomarker for immunotherapy for the patient, and wherein software, when executed by the processor core, causes the processor core to compute the eTMB values by:
generating a probabilistic model from Ribonucleic acid (RNA) sequence reads from an RNA sequence dataset,
where the TMB is a parameter of a prior distribution of the RNA sequence dataset, such that the probabilistic model has a TMB parameter; and
for each patient in the cohort, computing an eTMB value for the patient using the probabilistic model and based on a patient RNA sequence obtained from the patient;
combine a vector of eTMB values for the patients in the cohort with one or more other biomarkers and/or one or more molecular measurements for the patients in the cohort to obtain an eTMB signature for each patient;
train a function that estimates a likelihood of response to immunotherapy by applying a machine learning training method to the eTMB signatures; and
after training the function, for a new patient:
compute an eTMB value for the new patient by using the probabilistic model and based on a patient RNA sequence obtained from the new patient; and
apply the trained function to the eTMB signature of the new patient to estimate a patient likelihood of response to immunotherapy for the new patient,
wherein the eTMB signature is obtained by combining one or more biomarkers and/or one or more molecular measurements for the new patient with the eTMB value for the new patient.

5. The method of claim 1, wherein computing the eTMB value comprises fitting, by the
programmed processor, the probabilistic model to the patient RNA sequence data,
wherein fitting the probabilistic model to the patient RNA sequence data comprises computing an eTMB value for the patient,
wherein the eTMB value is computed as a value that maximizes a probability of observing the RNA sequence reads of the probabilistic model, assuming that the TMB parameter for the probabilistic model is the eTMB value.

6. The method of claim 5, wherein the probabilistic model is optimized to minimize disagreement between the eTMB value and a whole-exome-sequencing (WES)-based TMB value for the patient.

7. The method of claim 5, wherein fitting the probabilistic model to the patient RNA sequence data comprises employing an expectation-maximization optimization algorithm.

8. The method of claim 5, wherein the probabilistic model comprises a set of weights, and computing the eTMB value comprises optimizing the set of weights to maximize accuracy of the eTMB value for predicting response to immunotherapy over a set of patients.

9. The method of claim 8, wherein the set of weights models a contribution of each human gene transcript to the computation of the eTMB value.

10. The method of claim 1, wherein computing the eTMB value comprises computing, by the programmed processor, a summary statistic of a posterior probability distribution derived from the probabilistic model given the patient RNA sequence data.

11. The method of claim 1, wherein:
the eTMB value is a predictive biomarker for immunotherapy for the patient; and
the method further comprises administering immunotherapy to the patient upon a determination that the eTMB value for the patient meets or exceeds a threshold value.

12. The method of claim 11, wherein:
the eTMB value is a predictive biomarker for immune checkpoint inhibitor (ICPI) therapy for the patient; and
administering immunotherapy comprises immune checkpoint inhibitor (ICPI) therapy to the patient.

13. The method of claim 1, wherein the RNA sequence dataset is from subjects having a first disease, such that the probabilistic model is trained to be specific to the first disease.

14. The method of claim 13, wherein the first disease is a form of cancer.

15. The method of claim 1, wherein the probabilistic model is optimized to maximize an accuracy of the eTMB value for predicting response to immunotherapy over a set of patients.

16. The method of claim 1, wherein:
the RNA sequence reads comprise parts of transcripts; and
the eTMB value is computed by integrating mutation probabilities over all positions of all transcripts of the RNA sequence reads.

17. The method of claim 1, wherein the eTMB value is an estimate of mutated nucleotides in a transcriptome of the patient RNA sequence data.

18. The method of claim 1, further comprising computing, by the programmed processor, a confidence estimate for the computed eTMB value.

19. The method of claim 18, wherein:
generating the probabilistic model comprises generating a first probabilistic model; and
computing the confidence estimate comprises, repeatedly until a stopping criterion is met:
generating an additional probabilistic model by bootstrapping the RNA sequence reads used in the first probabilistic model; and
recomputing the eTMB value with the additional probabilistic model.

20. The computer system of claim 4, wherein the software, when executed by the processor core, causes the processor core to compute the eTMB value by fitting the probabilistic model to the patient RNA sequence,
wherein the eTMB value is computed as a value that maximizes a probability of observing the RNA sequence reads of the probabilistic model, assuming that the TMB parameter for the probabilistic model is the eTMB value.

21. The computer system of claim 4, wherein the software, when executed by the processor core, causes the processor core to compute the eTMB value by computing a summary statistic of a posterior probability distribution derived from the probabilistic model given the patient RNA sequence.

* * * * *